US 9,248,042 B2

(12) United States Patent
Lopez et al.

(10) Patent No.: US 9,248,042 B2
(45) Date of Patent: Feb. 2, 2016

(54) DORSAL FOOT SPLINT

(76) Inventors: Yessenia Lopez, Tarzana, CA (US);
Kenji Watabe, Ventura, CA (US);
Veneza Yuzon, Calabasas, CA (US);
Tracy E. Grim, Thousand Oaks, CA (US)

(*) Notice: Subject to any disclaimer, the term of this patent is extended or adjusted under 35 U.S.C. 154(b) by 206 days.

(21) Appl. No.: 13/612,623

(22) Filed: Sep. 12, 2012

(65) Prior Publication Data

US 2014/0074004 A1    Mar. 13, 2014

(51) Int. Cl.
*A61F 5/01* (2006.01)

(52) U.S. Cl.
CPC ..................................... *A61F 5/0113* (2013.01)

(58) Field of Classification Search
CPC ..................................................... A61F 5/0113
USPC .................... 602/28, 27, 23; 128/882; 482/79
See application file for complete search history.

(56) References Cited

U.S. PATENT DOCUMENTS

| | | | |
|---|---|---|---|
| 143,537 A | 10/1873 | Silberschmidt | |
| 1,472,415 A | 10/1923 | Haggerty | |
| 2,643,468 A | 6/1953 | Gottschalk | |
| 2,959,169 A | 11/1960 | Bless | |
| 3,464,126 A | 9/1969 | Sarkissian | |
| 3,504,668 A | 4/1970 | Boudon | |
| 3,527,209 A * | 9/1970 | Baker | 602/28 |
| 3,661,151 A | 5/1972 | Schoenbrun et al. | |
| 3,665,619 A | 5/1972 | Gray | |
| 3,792,537 A | 2/1974 | Plank et al. | |
| 3,805,773 A | 4/1974 | Sichau | |
| 3,814,088 A | 6/1974 | Raymond | |
| 3,955,565 A | 5/1976 | Johnson | |
| 3,976,059 A | 8/1976 | Lonardo | |
| 4,005,704 A | 2/1977 | Stöhr et al. | |
| 4,053,995 A | 10/1977 | Shein | |
| 4,057,056 A | 11/1977 | Payton | |
| 4,094,312 A | 6/1978 | Whyte | |
| 4,100,686 A | 7/1978 | Sgarlato et al. | |
| 4,100,918 A | 7/1978 | Glancy | |
| 4,184,273 A | 1/1980 | Boyer et al. | |
| 4,188,735 A | 2/1980 | Hahn | |
| 4,215,491 A | 8/1980 | Giannetti | |
| 4,217,706 A | 8/1980 | Vartanian | |
| 4,265,033 A | 5/1981 | Pois | |
| 4,268,931 A | 5/1981 | Salomon | |

(Continued)

FOREIGN PATENT DOCUMENTS

| CN | 201085714 Y | 7/2008 |
|---|---|---|
| CN | 201523712 U | 7/2010 |

(Continued)

OTHER PUBLICATIONS

PCT Publication No. WO/87/03471, dated Jun. 18, 1987, regarding PCT Application No. PCT/US86/02670.

(Continued)

*Primary Examiner* — Victoria J Hicks
(74) *Attorney, Agent, or Firm* — Arent Fox LLP

(57) ABSTRACT

A dorsal foot splint includes a dorsal member having a proximal portion for engaging the dorsal surface of the lower leg and a distal portion for engaging the dorsal surface of the foot. A tension strap is configured to adjust a position between the distal and proximal portions of the dorsal member to vary the tension applied to the plantar fascia and the Achilles tendon of a user.

11 Claims, 4 Drawing Sheets

(56) References Cited

U.S. PATENT DOCUMENTS

| | | |
|---|---|---|
| 4,393,866 A | 7/1983 | Finnieston |
| 4,446,856 A | 5/1984 | Jordan |
| 4,454,871 A | 6/1984 | Mann et al. |
| 4,494,536 A | 1/1985 | Latenser |
| 4,497,070 A | 2/1985 | Cho |
| 4,505,269 A | 3/1985 | Davies et al. |
| 4,510,927 A | 4/1985 | Peters |
| 4,550,721 A | 11/1985 | Michel |
| 4,556,054 A | 12/1985 | Paulseth |
| 4,559,934 A | 12/1985 | Philipp |
| 4,567,678 A | 2/1986 | Morgan et al. |
| 4,572,169 A | 2/1986 | Mauldin et al. |
| 4,587,962 A | 5/1986 | Greene et al. |
| 4,590,932 A | 5/1986 | Wilkerson |
| 4,624,247 A | 11/1986 | Ford |
| 4,628,945 A * | 12/1986 | Johnson, Jr. .................. 602/27 |
| 4,665,904 A | 5/1987 | Lerman |
| 4,771,768 A | 9/1988 | Crispin |
| 4,805,601 A | 2/1989 | Eischen, Sr. |
| 4,825,856 A | 5/1989 | Nelson |
| 4,844,094 A | 7/1989 | Grim |
| 4,862,900 A | 9/1989 | Hefele |
| 4,872,273 A | 10/1989 | Smeed |
| 4,879,822 A | 11/1989 | Hayes |
| 4,919,118 A | 4/1990 | Morris |
| 4,941,271 A | 7/1990 | Lakic |
| 4,947,838 A | 8/1990 | Giannetti |
| 4,964,402 A | 10/1990 | Grim et al. |
| 4,974,583 A | 12/1990 | Freitas |
| 4,982,733 A | 1/1991 | Broadhurst et al. |
| 4,999,932 A | 3/1991 | Grim |
| 5,020,523 A | 6/1991 | Bodine |
| 5,078,128 A | 1/1992 | Grim et al. |
| 5,086,761 A | 2/1992 | Ingram |
| 5,088,478 A | 2/1992 | Grim |
| 5,088,479 A | 2/1992 | Detoro |
| 5,088,481 A | 2/1992 | Darby |
| 5,092,321 A | 3/1992 | Spademan |
| 5,125,400 A | 6/1992 | Johnson, Jr. |
| 5,154,695 A | 10/1992 | Farris et al. |
| 5,176,623 A | 1/1993 | Stetman et al. |
| 5,197,942 A | 3/1993 | Brady |
| 5,213,564 A | 5/1993 | Johnson, Jr. et al. |
| 5,219,324 A | 6/1993 | Hall |
| 5,226,245 A | 7/1993 | Lamont |
| 5,226,875 A | 7/1993 | Johnson |
| 5,233,767 A | 8/1993 | Kramer |
| 5,242,379 A | 9/1993 | Harris et al. |
| 5,277,695 A | 1/1994 | Johnson, Jr. et al. |
| RE34,661 E | 7/1994 | Grim |
| 5,329,705 A | 7/1994 | Grim et al. |
| 5,330,419 A | 7/1994 | Toronto |
| 5,334,135 A | 8/1994 | Grim et al. |
| 5,352,189 A | 10/1994 | Schumann et al. |
| 5,353,525 A | 10/1994 | Grim |
| 5,367,789 A | 11/1994 | Lamont |
| 5,368,551 A | 11/1994 | Zuckerman |
| 5,370,133 A | 12/1994 | Darby et al. |
| 5,370,604 A | 12/1994 | Bernardoni |
| 5,378,223 A | 1/1995 | Grim et al. |
| 5,383,290 A | 1/1995 | Grim |
| 5,384,970 A | 1/1995 | Melton |
| 5,392,534 A | 2/1995 | Grim |
| 5,399,152 A | 3/1995 | Habermeyer et al. |
| 5,399,155 A | 3/1995 | Strassburg et al. |
| 5,407,421 A | 4/1995 | Goldsmith |
| 5,425,701 A | 6/1995 | Oster et al. |
| 5,426,872 A | 6/1995 | Hayes |
| 5,429,588 A | 7/1995 | Young et al. |
| 5,441,015 A | 8/1995 | Farley |
| 5,445,602 A | 8/1995 | Grim et al. |
| 5,460,599 A | 10/1995 | Davis et al. |
| 5,464,385 A | 11/1995 | Grim |
| 5,483,757 A | 1/1996 | Frykberg |
| 5,496,263 A | 3/1996 | Fuller, II et al. |
| 5,503,622 A | 4/1996 | Wehr |
| 5,507,720 A | 4/1996 | Lampropoulos |
| 5,526,586 A | 6/1996 | Foscaro |
| 5,527,269 A | 6/1996 | Reithofer |
| 5,551,950 A | 9/1996 | Oppen |
| 5,554,104 A | 9/1996 | Grim |
| 5,571,077 A | 11/1996 | Klearman et al. |
| 5,577,998 A | 11/1996 | Johnson, Jr. et al. |
| 5,582,579 A | 12/1996 | Chism et al. |
| 5,609,570 A | 3/1997 | Lamont |
| 5,617,650 A | 4/1997 | Grim |
| 5,620,411 A | 4/1997 | Schumann et al. |
| 5,632,723 A | 5/1997 | Grim |
| 5,641,322 A | 6/1997 | Silver et al. |
| 5,675,839 A | 10/1997 | Gordon et al. |
| 5,761,834 A | 6/1998 | Grim et al. |
| 5,762,622 A | 6/1998 | Lamont |
| 5,772,619 A | 6/1998 | Corbett |
| 5,776,090 A | 7/1998 | Bergmann et al. |
| 5,799,659 A | 9/1998 | Stano |
| 5,823,981 A | 10/1998 | Grim et al. |
| 5,827,210 A | 10/1998 | Antar et al. |
| 5,827,211 A | 10/1998 | Sellinger |
| 5,833,639 A | 11/1998 | Nunes et al. |
| 5,836,902 A | 11/1998 | Gray |
| 5,853,381 A | 12/1998 | Stevenson et al. |
| 5,857,987 A | 1/1999 | Habermeyer |
| 5,865,166 A | 2/1999 | Fitzpatrick et al. |
| 5,868,690 A | 2/1999 | Eischen, Sr. |
| 5,887,591 A | 3/1999 | Powell et al. |
| 5,891,073 A | 4/1999 | Deirmendjian et al. |
| 5,897,515 A | 4/1999 | Willner et al. |
| 5,897,520 A | 4/1999 | Gerig |
| 5,902,259 A | 5/1999 | Wilkerson |
| 5,913,841 A | 6/1999 | Lamont |
| 5,925,010 A | 7/1999 | Caprio, Jr. |
| 5,951,504 A | 9/1999 | Iglesias et al. |
| 5,954,075 A | 9/1999 | Gilmour |
| 5,961,477 A | 10/1999 | Turtzo |
| 5,980,475 A | 11/1999 | Gibbons |
| 5,993,404 A | 11/1999 | Mc Niel |
| 6,019,741 A | 2/2000 | Prieskorn |
| 6,021,780 A | 2/2000 | Darby |
| 6,024,712 A | 2/2000 | Iglesia et al. |
| 6,027,468 A | 2/2000 | Pick |
| 6,044,578 A | 4/2000 | Kelz |
| 6,056,712 A | 5/2000 | Grim |
| 6,126,625 A | 10/2000 | Lundberg |
| 6,154,983 A | 12/2000 | Austin et al. |
| 6,155,998 A | 12/2000 | Gilmour |
| 6,189,172 B1 | 2/2001 | Baek |
| 6,228,044 B1 | 5/2001 | Jensen et al. |
| 6,247,250 B1 | 6/2001 | Hauser |
| 6,267,742 B1 | 7/2001 | Krivosha et al. |
| 6,277,087 B1 | 8/2001 | Hess et al. |
| 6,282,816 B1 | 9/2001 | Rosendahl |
| 6,282,818 B1 | 9/2001 | Lu |
| 6,334,854 B1 | 1/2002 | Davis |
| 6,350,246 B1 | 2/2002 | DeToro |
| 6,361,514 B1 | 3/2002 | Brown et al. |
| 6,361,515 B1 | 3/2002 | Gilmour |
| 6,374,516 B1 | 4/2002 | Bonaventure et al. |
| 6,406,450 B1 | 6/2002 | Kowalczyk et al. |
| 6,409,695 B1 | 6/2002 | Connelly |
| 6,432,073 B2 | 8/2002 | Pior et al. |
| 6,491,654 B2 | 12/2002 | Lamont |
| D473,654 S | 4/2003 | Iglesias et al. |
| 6,558,339 B1 | 5/2003 | Graham |
| 6,572,571 B2 | 6/2003 | Lowe |
| 6,648,843 B1 | 11/2003 | Marciano et al. |
| 6,656,145 B1 | 12/2003 | Morton |
| 6,682,497 B2 | 1/2004 | Jensen et al. |
| 6,699,209 B2 | 3/2004 | Turtzo |
| 6,722,060 B2 | 4/2004 | Okajima |
| 6,755,798 B2 | 6/2004 | McCarthy et al. |
| 6,796,058 B2 | 9/2004 | Potchatko |
| D500,855 S | 1/2005 | Pick et al. |
| 6,866,043 B1 | 3/2005 | Davis |
| 6,923,780 B2 | 8/2005 | Price et al. |

(56) References Cited

U.S. PATENT DOCUMENTS

| | | |
|---|---|---|
| 6,945,946 B2 | 9/2005 | Rooney |
| 6,945,947 B2 | 9/2005 | Ingimundarson et al. |
| 6,955,654 B2 | 10/2005 | Gilmour |
| 6,976,972 B2 | 12/2005 | Bradshaw |
| 6,979,287 B2 | 12/2005 | Elbaz et al. |
| 6,991,613 B2 | 1/2006 | Sensabaugh |
| 7,018,351 B1 | 3/2006 | Iglesias et al. |
| 7,018,352 B2 | 3/2006 | Pressman et al. |
| D519,211 S | 4/2006 | Doty et al. |
| 7,077,818 B2 | 7/2006 | Ingimundarson et al. |
| 7,094,213 B1 * | 8/2006 | Cook .................. 602/65 |
| 7,163,518 B1 | 1/2007 | Roche et al. |
| 7,163,519 B2 | 1/2007 | Price et al. |
| 7,182,743 B2 | 2/2007 | Slautterback et al. |
| D541,085 S | 4/2007 | Marsilio |
| 7,288,076 B2 | 10/2007 | Grim et al. |
| 7,294,114 B1 | 11/2007 | Clement et al. |
| 7,303,538 B2 | 12/2007 | Grim et al. |
| 7,311,686 B1 | 12/2007 | Iglesias et al. |
| 7,354,411 B2 | 4/2008 | Perry et al. |
| 7,384,584 B2 | 6/2008 | Jerome et al. |
| 7,475,501 B1 | 1/2009 | DeToro et al. |
| 7,563,238 B1 | 7/2009 | Breashears |
| 7,569,022 B2 | 8/2009 | Morinaka |
| 7,585,285 B2 | 9/2009 | Pone et al. |
| 7,597,674 B2 | 10/2009 | Hu et al. |
| 7,666,157 B2 | 2/2010 | Win |
| D616,556 S | 5/2010 | Hu |
| 7,727,173 B2 | 6/2010 | Rooney |
| 7,727,174 B2 | 6/2010 | Chang et al. |
| 7,743,532 B2 | 6/2010 | Bledsoe et al. |
| D619,726 S | 7/2010 | Win |
| 7,758,529 B2 | 7/2010 | Jensen et al. |
| 7,867,182 B2 | 1/2011 | Iglesias et al. |
| D634,438 S | 3/2011 | Hu |
| 7,896,826 B2 | 3/2011 | Hu et al. |
| 7,918,813 B2 | 4/2011 | Drake et al. |
| D640,792 S | 6/2011 | Anderson et al. |
| D641,084 S | 7/2011 | Anderson et al. |
| D642,695 S | 8/2011 | Anderson et al. |
| 8,002,724 B2 | 8/2011 | Hu et al. |
| D645,153 S | 9/2011 | Anderson et al. |
| 8,012,112 B2 | 9/2011 | Barberio |
| D662,598 S | 6/2012 | Anderson et al. |
| 8,226,585 B2 | 7/2012 | Pick et al. |
| 8,251,932 B2 | 8/2012 | Fout |
| 8,251,936 B2 | 8/2012 | Fout et al. |
| 2002/0062579 A1 | 5/2002 | Caeran |
| 2002/0128574 A1 | 9/2002 | Darby |
| 2003/0196352 A1 | 10/2003 | Bledsoe et al. |
| 2004/0015112 A1 | 1/2004 | Salutterback et al. |
| 2004/0030275 A1 | 2/2004 | Morinaka |
| 2005/0172517 A1 | 8/2005 | Bledsoe et al. |
| 2005/0228332 A1 | 10/2005 | Bushby |
| 2005/0240133 A1 | 10/2005 | Rooney |
| 2005/0274046 A1 | 12/2005 | Schwartz |
| 2006/0032093 A1 | 2/2006 | Vannini |
| 2006/0048344 A1 | 3/2006 | Cavanagh et al. |
| 2006/0084899 A1 | 4/2006 | Verkade et al. |
| 2006/0189907 A1 | 8/2006 | Pick et al. |
| 2006/0217649 A1 | 9/2006 | Rabe |
| 2007/0010770 A1 | 1/2007 | Gildersleeve |
| 2007/0191749 A1 | 8/2007 | Barberio |
| 2007/0260164 A1 | 11/2007 | Chiodo et al. |
| 2007/0276307 A1 | 11/2007 | Erenstone |
| 2008/0004558 A1 | 1/2008 | Outred et al. |
| 2008/0098626 A1 | 5/2008 | Wright |
| 2008/0154166 A1 | 6/2008 | Beckwith et al. |
| 2008/0294082 A1 | 11/2008 | Chang et al. |
| 2008/0294083 A1 | 11/2008 | Chang et al. |
| 2008/0302371 A1 | 12/2008 | Cohen et al. |
| 2008/0319362 A1 | 12/2008 | Joseph |
| 2009/0043234 A1 | 2/2009 | Bledsoe et al. |
| 2009/0076425 A1 | 3/2009 | Schwartz |
| 2009/0192427 A1 | 7/2009 | Brown et al. |
| 2009/0192428 A1 | 7/2009 | DeBoer et al. |
| 2009/0227927 A1 | 9/2009 | Frazer |
| 2009/0227928 A1 * | 9/2009 | Drake et al. .................. 602/28 |
| 2009/0264803 A1 | 10/2009 | Darby, II et al. |
| 2009/0299246 A1 | 12/2009 | Pone et al. |
| 2009/0306565 A1 | 12/2009 | Chan |
| 2010/0069807 A1 | 3/2010 | Cox |
| 2010/0204631 A1 | 8/2010 | Rooney |
| 2010/0234782 A1 | 9/2010 | Hu et al. |
| 2010/0324461 A1 | 12/2010 | Darby |
| 2011/0015555 A1 | 1/2011 | Anderson et al. |
| 2011/0021963 A1 | 1/2011 | Graddon et al. |
| 2011/0034844 A1 * | 2/2011 | Thorgilsdottir et al. ........ 602/18 |
| 2011/0066095 A1 | 3/2011 | Price et al. |
| 2011/0146032 A1 | 6/2011 | Hu et al. |
| 2011/0196275 A1 | 8/2011 | Chang et al. |
| 2011/0313336 A1 | 12/2011 | Chan |
| 2012/0000092 A1 | 1/2012 | Ingvarsson et al. |
| 2012/0010534 A1 | 1/2012 | Kubiak et al. |
| 2012/0010535 A1 | 1/2012 | Kubiak et al. |
| 2012/0035520 A1 | 2/2012 | Ingimundarson et al. |
| 2012/0065564 A1 | 3/2012 | Hoffmeier et al. |
| 2012/0078148 A1 | 3/2012 | Hu et al. |
| 2012/0116275 A1 | 5/2012 | Pochatko |
| 2013/0066247 A1 | 3/2013 | Bird et al. |

FOREIGN PATENT DOCUMENTS

| | | |
|---|---|---|
| DE | 2341658 | 3/1974 |
| DE | 3228753 | 2/1984 |
| DE | 3909922 | 2/1990 |
| EP | 0095396 | 11/1983 |
| EP | 1006960 | 1/2003 |
| FR | 2399811 | 3/1979 |
| RU | 2165229 | 4/2001 |

OTHER PUBLICATIONS

Article from http://www.alimed.com regarding AliMed D2 Night Splint for Plantar Fasciitis.
Aircast Incorporated Product Brochure, "SP-Walker, short pneumatic walking brace", Jan. 11, 2002.
PCT Publication No. WO/2012/020251, dated Feb. 16, 2012, regarding PCT Application No. PCT/GB2011/051499.
PCT Publication No. WO/2005/097014, dated Oct. 20, 2005, regarding PCT Application No. PCT/SE2005/000513.
PCT Publication No. WO/2012/099989, dated Jul. 26, 2013, regarding PCT Application No. PCT/US2012/021763.
PCT Publication No. WO/2012/001678, dated Jan. 5, 2012, regarding PCT Application No. PCT/IL2011/000487.
Paul A. Dale, M.D. et al.; "A New Concept in Fracture Immobilization", Clinical Orthopaedics. Oct. 1993, vol. 295: 264-269.
European Search Report and Opinion dated Sep. 13, 2013, regarding EP13184215.
EP Communication dated Jun. 12, 2015, regarding EP13184215.5.

* cited by examiner

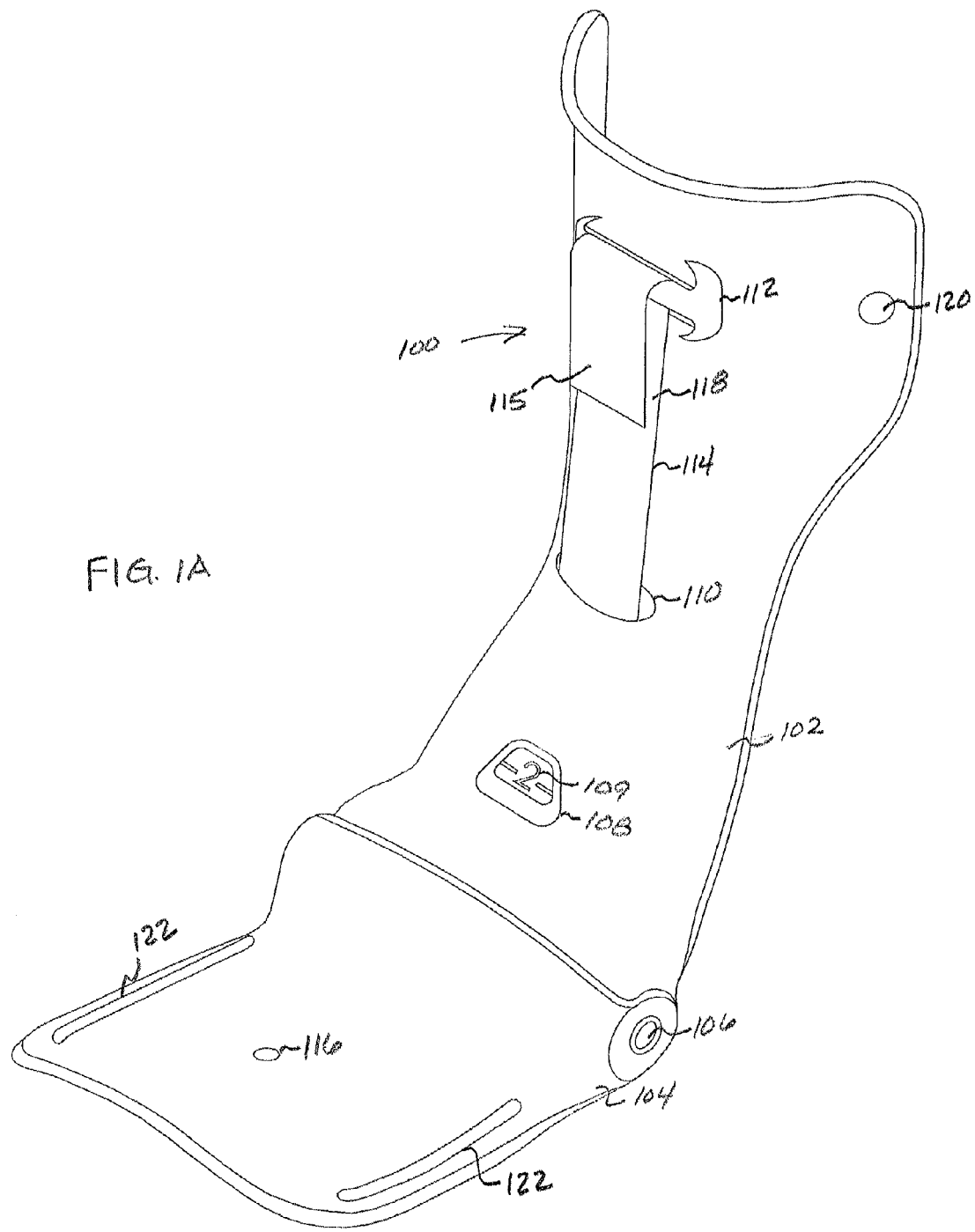

DORSAL FOOT SPLINT

BACKGROUND

1. Field

The present disclosure relates generally to orthotics, and more specifically to dorsal foot splints.

2. Background

The plantar fascia is a thick tissue that connects the heal bone to the toes and creates the arch of the foot. Excessive wear of the plantar fascia often results in an inflammatory condition known as plantar fasciitis. Plantar fasciitis is the most common source of pain on the bottom of the heel. Approximately two million patients are treated for this condition every year.

A common therapeutic treatment for plantar fascia is physical therapy. Physical therapy typically includes stretching the planar fascia and Achilles tendon and strengthening the lower leg muscles. More aggressive treatments include painful injections into the heel of the foot. Night splints may also be used to treat plantar fasciitis by keeping the foot in a dorsi-flexed position to stretch the plantar fascia and the Achilles tendon. One example of a night splint is a dorsal foot splint. The dorsal foot splint rests against the dorsal surface of the lower leg and foot leaving the heel and the back of the lower leg exposed. This design tends to be more comfortable than other night splints, such as the posterior foot splint. As a result, the dorsal foot splint is more likely to be worn at night over an extended period, thereby facilitating a speedy recovery.

The dorsal foot splint has its drawbacks, however. The dorsal foot splint supports the lower leg and foot from the top with a continuous rigid splint member. Accordingly, the tension applied to the plantar fascia and Achilles tendon is fixed. A posterior foot splint, on the other hand, supports the foot from below and the leg from behind. Tension straps between the foot portion and the posterior leg portion of the splint allow the user to adjust the tension applied to the plantar fascia and Achilles tendon. Although there have been some attempts in the past to develop a dorsal foot splint that can vary the tension applied to the plantar fascia and Achilles tendon, these foot splints are bulky, difficult to apply, and provide limited range of motion. Accordingly, there is a need in the art for a new innovative design that combines the adjustability of the posterior foot splint with the comfort of a dorsal foot splint.

SUMMARY

Various aspects of dorsal foot splints will be described more fully hereinafter in the detailed description of this disclosure.

One aspect of a dorsal foot splint includes a dorsal member having a proximal portion for engaging the dorsal surface of the lower leg and a distal portion for engaging the dorsal surface of the foot, a tension strap configured to adjust a position between the distal and proximal portions of the dorsal member, wherein the dorsal member comprises an aperture, and wherein an indication of the position is viewable through the aperture.

Another aspect of a dorsal foot splint includes a dorsal member having a proximal portion for engaging the dorsal surface of the lower leg and a distal portion for engaging the dorsal surface of the foot, and a tension strap configured to adjust a position between the distal and proximal portions of the dorsal member, the tension strap extending between the distal and proximal portions of the dorsal member along an interior of the dorsal member from an attachment point on the distal portion to a strap hole in the proximal portion.

One aspect of a method for treating plantar fasciitis uses a dorsal foot splint having a dorsal member. The method includes applying the dorsal foot splint to a user by securing a proximal portion of the dorsal member to the dorsal surface of the lower leg of the user and a distal portion of the dorsal member to the dorsal surface of the foot; and adjusting a position between the proximal and distal portions of the dorsal member portion to a desired position based on indicia viewed through an aperture in the dorsal member.

It is understood that other aspects of apparatuses, methods, and articles of manufacture will become readily apparent to those skilled in the art from the following detailed description, wherein various aspects of apparatuses, methods and articles of manufacture are shown and described by way of illustration. As will be realized, these aspects may be implemented in various forms and its details are capable of modification in various other respects. Accordingly, the drawings and detailed description are to be regarded as illustrative in nature and not as restrictive.

BRIEF DESCRIPTION OF THE DRAWINGS

The accompanying drawings are not intended to be drawn to scale. In the drawings, each identical or nearly identical component that is illustrated in various figures is represented by a like numeral. For purposes of clarity, not every component may be labeled in every drawing. Various aspects of dorsal foot splints will be described more fully hereinafter with reference to the accompanying drawings, in which:

FIG. 1A is a front perspective view illustrating an example of a dorsal member for a dorsal foot splint for treating plantar fasciitis and other related conditions;

DETAILED DESCRIPTION

Various aspects of the invention will be described more fully hereinafter with reference to the accompanying drawings. The invention, however, may be embodied in many different forms by those skilled in the art and should not be construed as limited to any specific structure or function presented herein. Rather, the various aspects of the invention are provided so that this disclosure will be thorough and complete, and will fully convey the scope of the invention to those skilled in the art. Accordingly, the detailed description and drawings are merely illustrative of the disclosure rather than limiting, the scope of the disclosure being defined by the appended claims and equivalents thereof.

Various aspects of the present invention will now be presented with reference to a dorsal foot splint and method of using the splint for treating plantar fasciitis and other related conditions. One embodiment of a dorsal foot splint includes a dorsal member having a proximal portion for engaging the dorsal surface of the lower leg and a distal portion for engaging the dorsal surface of the foot. The proximal portion of the dorsal member may be pivotally connected to the distal portion of the dorsal member to allow a user to adjust the position between the lower leg and the foot, and thereby adjust the tension applied to the plantar fascia and the Achilles tendon.

A tension strap may be used to adjust the position between the distal and proximal portions. A tension indicator corresponding to the position between the distal and proximate portions of the dorsal member may be viewed by a user through an aperture in the dorsal member during this process.

Figure 1B:
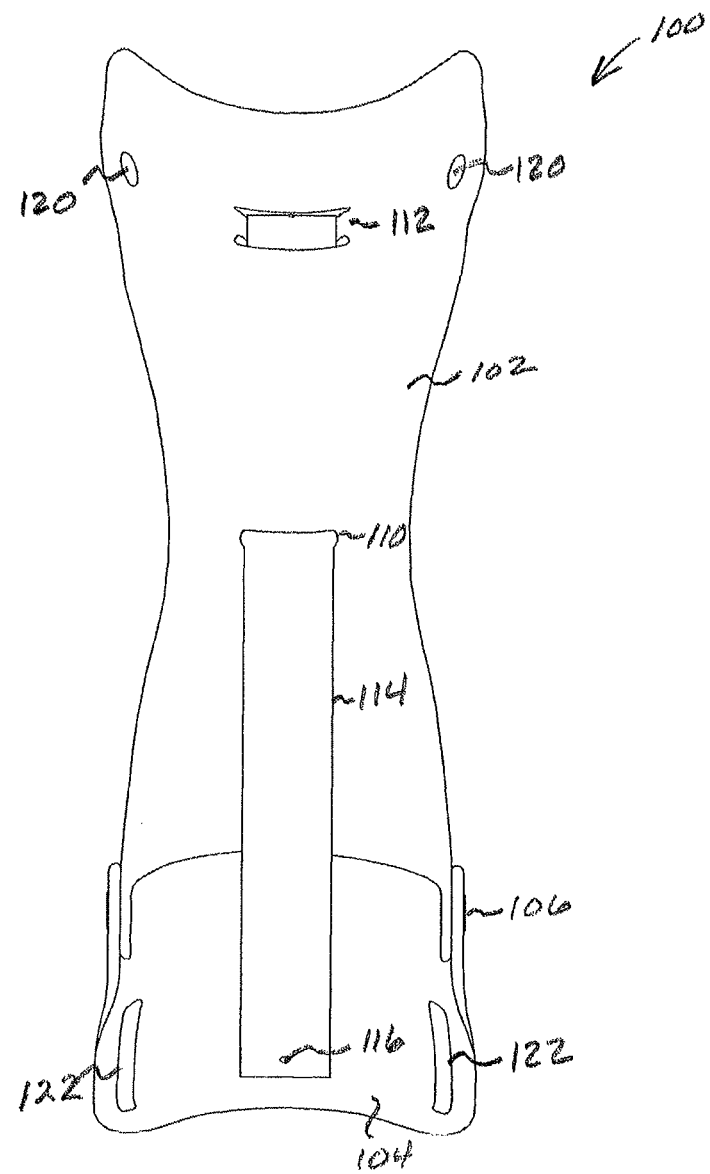
FIG. 1B is a rear view of the dorsal member of FIG. 1A.

Referring to FIGS. 1A and 1B, the dorsal member 100 of the dorsal foot splint includes a proximal portion 102 and a distal portion 104. The proximal portion 102 and the distal portion 104 may be formed from a thermoplastic material processed by any number of techniques, including by way of example, injection molding, extrusion, or any other suitable process. Examples of thermoplastic materials may include polystyrene, polyethylene, acrylic, polypropylene, polyester, polyamide, polyvinyl chloride, phenol formaldehyde and/or the like. Alternatively, the proximal and distal portions may be formed from a wide variety of other suitable materials depending on the particular application and the medical condition being treated. The proximal portion 102 of the dorsal member 100 may be coupled to the distal portion 104 of the dorsal member 100 by connectors 106 on the medial and lateral sides of the dorsal member 100. The connectors allow the two portions to pivot with respect to one another. The connectors 106 may be hinges, pins, rivets, dowels, or any other suitable pivotal connector component. Alternatively, the proximal and dorsal portions may be connected with a sliding hinge that allows the proximal and distal portions to slide with respect to one another to adjust the tension applied to the plantar fascia and the Achilles tendon.

The dorsal foot splint may also include a tension indicator to assist the user in adjusting the tension to the plantar fascia and the Achilles tendon. In one embodiment, the tension indicator may include an aperture 108 in the dorsal member 100 through which a user may view indicia 109 corresponding to the position between the proximal and distal portions of the dorsal member 100. This configuration may assist the user in setting the appropriate tension to the plantar fascia and Achilles tendon to optimize the therapeutic benefits of the device while managing pain. By way of example, a user may use the tension indicator to initially set the position between the proximal and distal portions of the dorsal member 100 to apply a certain tension to the plantar fascia and Achilles tendon. The initial setting may thereafter serve as a reference for adjusting the position between the two portions to gradually increase the tension as the treatment progresses. The aperture 108 is shown in the proximal portion 102 of the dorsal member, but alternatively may be formed in the distal portion 104.

The proximal portion 102 of the dorsal member 100 is also shown with a strap hole 110 and a pivot bar 112. A tension strap 114 extends between the distal portion 104 and the proximal portion 102. The tension strap 114 may be attached to the interior portion of the distal portion 104 by an anchor point 116 such as a rivet or any other suitable means. In the embodiment shown, the tension strap 114 extends from the anchor point 116 along the interior of the dorsal member 100, out the strap hole 110, along the exterior of the dorsal member 100, and through the pivot bar 112. The position between the proximal and distal portions of the dorsal member 100 may then be adjusted by pulling on the upper end 115 of the tension strap 114 extending from the pivot bar 112. The upper end 115 of the tension strap 112 may then be fastened to the mid-portion 118 of the tension strap 114 below the pivot bar 112 to secure the position set by the user between the foot and the leg. The means of attachment may be hook and loop fasteners sold under the trademark "Velcro," or any other means that provides a removable attachment between the two. This configuration provides a low profile design that is easy to use.

Although a pulley system has been described in conjunction with one embodiment of a dorsal foot splint, other systems may be used for adjusting the tension applied to the plantar fascia and Achilles tendon of the user. Those skilled in the art will be readily able to design the optimal means for adjusting the tension of the splint depending on the particular treatment required and the intended user.

The dorsal member 100 may also include holes 120 on the medial and lateral sides of the proximal portion 102. The holes 120 may be used to support D-rings (not shown) for a calf strap (not shown). In a manner to be described in more detail later, the calf strap may be used to secure the users leg to the dorsal foot splint.

The dorsal member 100 is also shown with slits 122 on the medial and lateral sides of the distal portion 104. The slits 122 provide a means for air flow to the foot positioned below the dorsal member 100 to improve user comfort. Alternatively, the slits 122 may be configured to receive additional straps to support additional padding. By way of example, a pneumatic bladder on the interior portion of the dorsal member may include straps supported by the slits 122.

Figure 2:
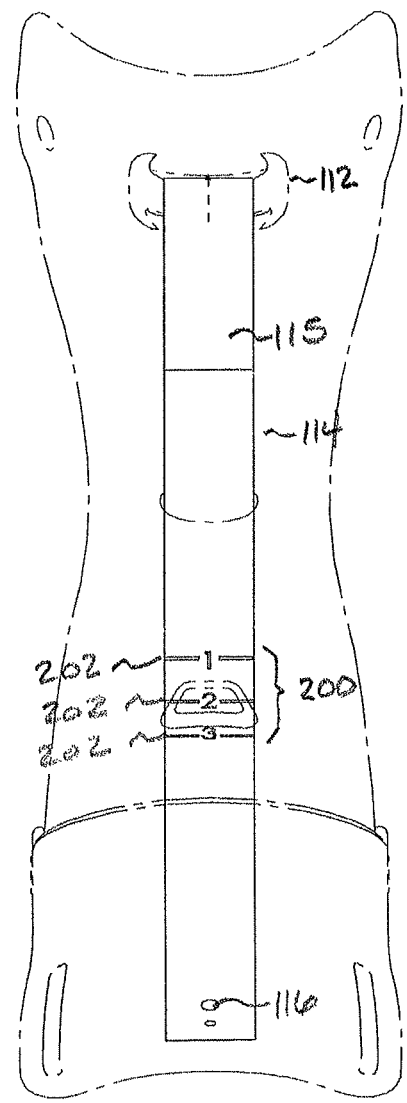
FIG. 2 is a phantom front view of the dorsal member of FIG. 1A illustrating an example of indicia which may be used to assist the user in setting the proper position between the lower leg and the foot.

As described above, a tension indicator may be used to assist the user in setting the proper position between the leg and the foot to optimize the therapeutic benefit of the device while managing pain. The tension indicator may include an aperture 108 in the dorsal member 100 through which a user may view indicia 109 corresponding to the position between the proximal and distal portions of the dorsal member 100. Referring to FIG. 2, the indicia may take the form of an indicator segment 200 attached to the tension strap 114 below the mid-portion 118. The indicator segment 200 may be printed with numerical indicators 202 that extend sequentially along the interior of the dorsal member 100 from just below the mid-portion 118 of the tension strap 114 toward the anchor point 116. The indicator segment 200 may also be aligned with the aperture 108 in the dorsal member 100 such that different numerical indicators 202 are pulled past the aperture 108 as the tension strap 114 is pulled through the pivot bar 112. By way of example, the indicator segment 200 may include numerical indicators 202 comprising "1", "2", and "3". In this example, the number "1" is positioned on the indicator segment 200 below the upper end 115 of the tension strap 114, the number "2" is positioned below number "1" on the indicator segment 200, closer to the anchor point 116, and the number "3" is positioned on the indicator segment 200 below that, closest to the anchor point 116. With this arrangement, the user may pull the tension strap 114 through the pivot bar 112 until the number "1" appears in the aperture 108, resulting in a position between the leg and foot that results in minimal tension to the plantar fascia and Achilles tendon. The user may then pull the tension strap 114 further through the pivot bar 112 until the number "2" appears in the aperture 108, thereby providing a greater tension to the plantar fascia and Achilles tendon. The user may then achieve maximum tension by further pulling the tension strap 114 through the pivot bar 112 until the number "3" appears in the aperture 108.

Alternatively, the indicator segment 200 may include informational indicators comprising, by way of example, "MINIMUM", "90°", and "MAXIMUM". In this example, the "MINIMUM" indicator would be positioned on the indicator segment 200 below the upper end 115 of the tension strap 114, the "90°" indicator would be positioned below the "MINIMUM" indicator on the indicator segment 200, closer to the anchor point 116, and the "MAXIMUM" indicator would be positioned on the indicator segment 200 below that, closest to the anchor point 116. With this arrangement, the user may pull the tension strap 114 through the pivot bar 112 until the "MINIMUM" indicator appears in the aperture 108, resulting in a position between the leg and foot that results in minimal tension to the plantar fascia and Achilles tendon. The user may then pull the tension strap 114 further through the pivot bar 112 until the "90°" indicator appears in the aperture 108, thereby providing a greater tension to the plantar fascia and Achilles tendon by applying a 90° angle between the foot and the leg. The user may then achieve maximum tension by further pulling the tension strap 114 through the pivot bar 112 until the "MAXIMUM" indicator appears in the aperture 108.

Figure 3:
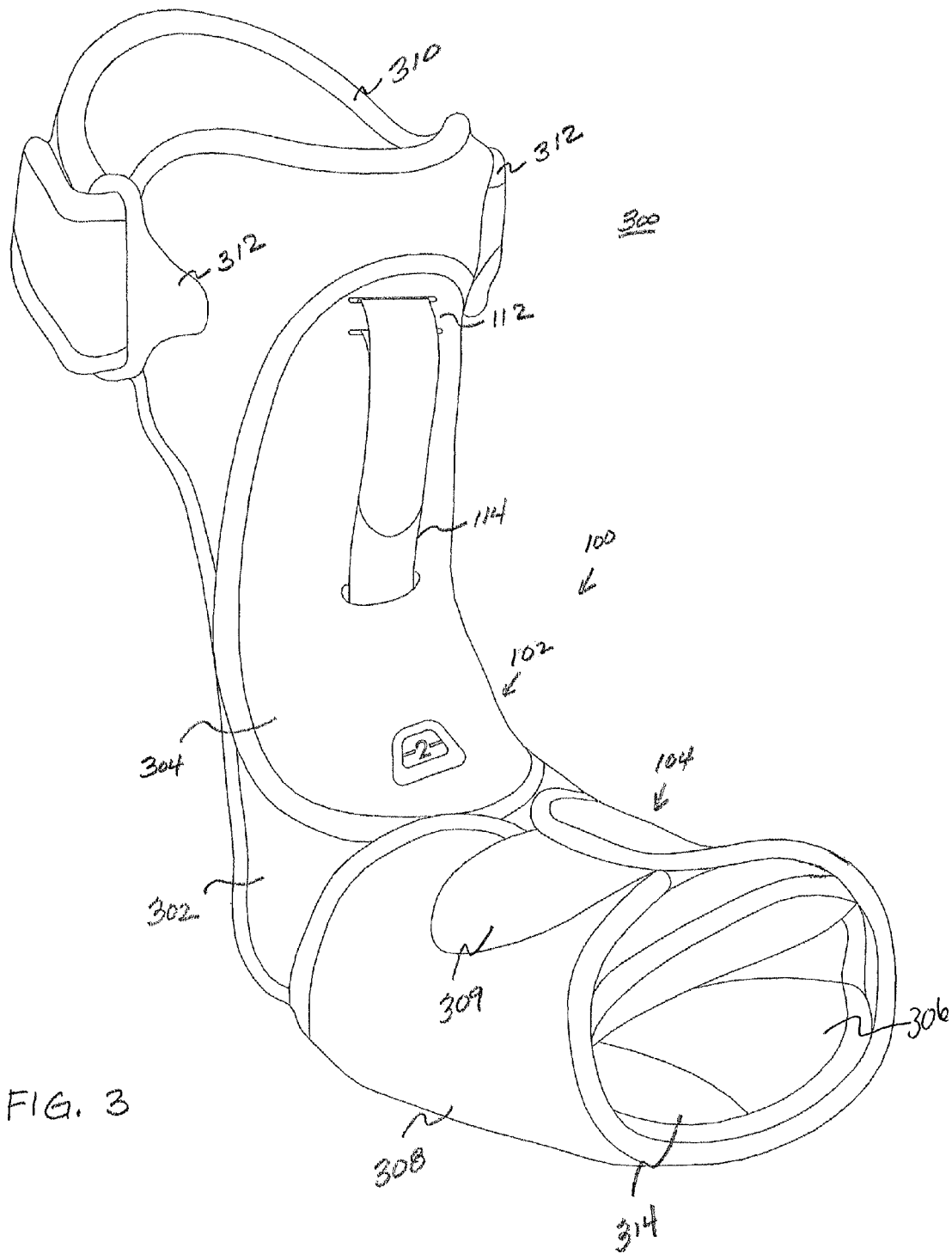
FIG. 3 is a perspective view illustrating an example of a dorsal foot splint.

Referring to FIG. 3, the dorsal foot splint 300 may be designed to be comfortably and adjustably worn by the user. As described above, the dorsal foot splint 300 includes a dorsal member 100 comprising a proximal portion 102 for positioning on the dorsal side of the lower leg and a distal portion 104 for positioning on the dorsal side of the foot. A cloth cover 302 may be situated over the dorsal member 100. In the embodiment shown, the cloth cover 302 is a single or multiple piece material that covers both the exterior and interior portions of the dorsal member 100. The portion of the cover 302 on the exterior portion of the dorsal member 100 is shown with a cut-out portion 304 that provides the user with access to the tension strap 114. The cut-out portion 304 also allows the user to view the tension indicator through the aperture as he or she pulls the tension strap 114 through the pivot bar 112 to adjust the position between the proximal and distal portions of the dorsal member 100.

The distal portion 104 of the dorsal member 100 is shown with a support member 306 for the ball of the foot. The support member 306 extends from the medial and lateral sides of the cover 302 on the distal portion 104 of the dorsal member 100 and is configured to receive the foot. The support member 306 may be a soft, durable padding material that provides comfort to the user during use. In one embodiment of the dorsal foot splint, the support member 306 may include a soft, durable padding material at the sole of the foot to provide user comfort with elastic material extending down the medial and lateral sides of the foot to accommodate different size feet. In some embodiments, a rigid member (not shown) may be attached to the bottom of the support member 306 to better support the metatarsals of the user's foot.

A foot strap 308 may be used to secure the user's foot to the dorsal splint. The foot strap 308 may take on various forms depending on the particular application and intended user. In the embodiment shown, the foot strap 306 surrounds the distal portion 106 of the dorsal member 100 and the support member 306. As described in connection with the tension strap above, the foot strap 308 may include a fastening material on a tab 309 that is formed to releasably mate with fastening material on the exterior of the foot strap 308, which may be hook and loop material sold under the trademark "Velcro," or any other means that allows the user to adjust the tension of the foot strap 308 around the foot.

The proximal portion 102 of the dorsal member 100 is held to the user's foot by a calf strap 310. Similar to the foot strap 308, the calf strap 310 may take on various forms depending on the particular application and intended user. By way of example, the calf strap 310 may be wrapped around and secured to the lower leg of the user with a strap and D-ring configuration as shown in FIG. 3. The D-rings provide a pivotal function to better accommodate user's with different size calves. In this example, D-rings 312 on the medial and lateral sides of the dorsal member 100 are attached to the proximal portion 102 by rivets (not shown) through holes 120 (see FIG. 1A) or other suitable means. One end of the calf strap 310 may be attached to a D-ring 312 at the medial side of the dorsal member 100 with the other end of the calf strap 310 free to extend around the user's calf to the D-ring 312 at the lateral side of the dorsal member 100. The user may then adjust the tension of the calf strap 310 around his or her calf by pulling the end of the calf strap through the D-ring 312 on the lateral side of the dorsal member and then attaching the end to the mid-portion of the calf strap 310. The means of attachment may be hook and loop fasteners sold under the trademark "Velcro," or any other means that provides a removable attachment between the two.

The interior portion of the cover 306 may have a soft, durable padding material 314 that protects the leg and foot of the user from the dorsal member 100. The padding material may be a single continuous piece covering the interior of the cover 306 or multiple pieces. The padding material may be a single layer or multiple layers for increased comfort. Various methods of padding the dorsal splint may be implemented depending upon the particular application and the intended user.

The previous description is provided to enable any person skilled in the art to fully understand the full scope of the present invention. Modifications to the various configurations disclosed herein will be readily apparent to those skilled in the art. Thus, the claims are not intended to be limited to the various aspects of the disclosure described herein, but are to be accorded the full scope consistent with the language of claims. All structural and functional equivalents to the components of the various embodiments described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for."

What is claimed is:

1. A dorsal foot splint, comprising:
   a dorsal member having a proximal portion for engaging the lower leg and a distal portion for engaging the foot, the dorsal member having an aperture; and
   a tension strap to adjust a position between the distal and proximal portions of the dorsal member, the tension strap comprising a plurality of spaced apart indicators, each of the indicators when viewed through the aperture corresponding to a different position between the distal and proximal portions as the tension strap is manipulated,
   wherein the tension strap extends from an attachment point on the distal portion to a strap hole in the proximal portion,
   wherein the entire length of the tension strap between the attachment point and the aperture is positioned along an interior of the dorsal member,
   wherein the entire length of the tension strap between the aperture and the strap hole is positioned along the interior of the dorsal member, and
   wherein the plurality of spaced apart indicators are positioned on the tension strap such that only one indicator of the plurality of spaced apart indicators is viewable at a time in use.

2. The dorsal foot splint of claim 1 wherein the tension strap extends between the distal and proximal portions of the dorsal member.

3. The dorsal foot splint of claim of claim 2 wherein the proximal portion of the dorsal member comprises a pivot bar, and wherein the tension strap extends along an exterior of the proximal portion from the strap hole to the pivot bar.

4. The dorsal foot splint of claim 3 wherein the position between the proximal and distal portions of the dorsal member is adjusted by pulling the tension strap through the pivot bar.

5. The dorsal foot splint of claim 1 wherein the aperture is formed in the proximal portion of the dorsal member.

6. The dorsal foot splint of claim 1 wherein the dorsal member further comprises a support member to support the ball of the foot, the support member having a rigid member to support the metatarsals of the foot.

7. The dorsal foot splint of claim 1 wherein the dorsal member further comprises first and second D-rings on the medial and lateral sides, respectively, of the proximal portion of the dorsal member, the dorsal member further comprising a calf strap configured to extend around the calf of the user between the first and second D-rings.

8. A method for treating plantar fasciitis using a dorsal foot splint having a dorsal member, comprising:
 applying the dorsal foot splint to a user by securing a proximal portion of the dorsal member to the lower leg of the user and a distal portion of the dorsal member to the foot, the dorsal foot splint comprising:
 an aperture; and
 a tension strap to adjust a position between the proximal and distal portions, the tension strap having spaced apart indicia, each of the spaced apart indicia when viewed through the aperture corresponding to a different position between the distal and proximal portions as the tension strap is manipulated,
 wherein the tension strap extends from an attachment point on the distal portion to a strap hole in the proximal portion,
 wherein the entire length of the tension strap between the attachment point and the aperture is positioned along an interior of the dorsal member,
 wherein the entire length of the tension strap between the aperture and the strap hole is positioned along the interior of the dorsal member, and
 wherein the spaced apart indicia are positioned on the tension strap such that only one indicia of the spaced apart indicia is viewable at a time in use; and
 adjusting a position between the proximal and distal portions of the dorsal member portion to a desired angle based on an indicia viewed through the aperture.

9. The method of claim 8 wherein the aperture is formed in the proximal portion of the dorsal member.

10. The method of claim 9 wherein the proximal portion of the dorsal member comprises a pivot bar, and wherein the tension strap extends along an exterior of the proximal portion from the strap hole to the pivot bar.

11. The dorsal foot splint of claim 10 wherein the desired angle between the proximal and distal portions of the dorsal member is adjusted by pulling the tension strap through the pivot bar.

* * * * *